(12) United States Patent
Schaner et al.

(10) Patent No.: US 8,371,303 B2
(45) Date of Patent: Feb. 12, 2013

(54) SYSTEM AND METHOD FOR IMAGING ENDOTRACHEAL TUBE PLACEMENT AND MEASURING AIRWAY OCCLUSION CUFF PRESSURE

(75) Inventors: David Schaner, New York, NY (US); Harshvardhan N. Chaobal, New York, NY (US)

(73) Assignee: Anesthetech Inc., New York, NY (US)

( * ) Notice: Subject to any disclaimer, the term of this patent is extended or adjusted under 35 U.S.C. 154(b) by 278 days.

(21) Appl. No.: 12/851,059

(22) Filed: Aug. 5, 2010

(65) Prior Publication Data

US 2011/0030694 A1 Feb. 10, 2011

Related U.S. Application Data

(60) Provisional application No. 61/231,631, filed on Aug. 5, 2009.

(51) Int. Cl.
*A61M 16/00* (2006.01)
*A61B 5/04* (2006.01)
*A61B 5/00* (2006.01)
*A61B 5/103* (2006.01)
*A61B 5/107* (2006.01)

(52) U.S. Cl. ......... 128/207.15; 128/200.24; 128/204.18; 128/204.21; 128/204.22; 128/204.23; 128/205.23; 128/207.14; 600/309; 600/311; 600/372; 600/373; 600/380; 600/393; 600/420; 600/421; 600/424; 600/425; 600/427; 600/431; 600/433; 600/434; 600/435; 600/437; 600/438; 600/443; 600/444; 600/445; 600/449; 600/459; 600/462; 600/463; 600/466; 600/470; 600/488; 600/552; 600/593; 604/505; 604/66; 604/100.01; 604/100.02; 604/100.03

(58) Field of Classification Search .................. None
See application file for complete search history.

(56) References Cited

U.S. PATENT DOCUMENTS

| | | | |
|---|---|---|---|
| 4,856,993 A | 8/1989 | Maness | |
| 5,785,051 A | 7/1998 | Lipscher | |
| 5,865,801 A | 2/1999 | Houser | |
| 6,004,269 A | 12/1999 | Crowley | |

OTHER PUBLICATIONS

International Search Report and Written Opinion of the International Searching Authority, both with a mailing date of Nov. 15, 2010, issued in related PCT Application No. PCT/US2010/044562.

*Primary Examiner* — Melanie Hand
*Assistant Examiner* — Joshua Lee
(74) *Attorney, Agent, or Firm* — Jeffer Mangels Butler & Mitchell LLP

(57) ABSTRACT

Described herein is an apparatus that includes an endotracheal tube or airway device having a proximal end and a distal end and an occlusion cuff. The occlusion cuff includes a sensor for helping determine proper endotracheal or airway device placement.

14 Claims, 7 Drawing Sheets

SYSTEM AND METHOD FOR IMAGING ENDOTRACHEAL TUBE PLACEMENT AND MEASURING AIRWAY OCCLUSION CUFF PRESSURE

This application claims the benefit of U.S. Provisional Application No. 61/231,631, filed Aug. 5, 2009, which is herein incorporated by reference in its entirety.

FIELD OF THE INVENTION

The present invention relates to endotracheal tubes, and, more particularly, to an endotracheal tube having a sensor in the airway occlusion cuff.

BACKGROUND OF THE INVENTION

Existing methods to verify the proper positioning of an endotracheal tube (ETT) have been shown to have limited sensitivity and specificity. There are two strategies used to determine ETT placement: methods that detect the physiological results of moving air through the ETT and methods that attempt to detect the location of the ETT using imaging and/or that exploit the inherent characteristics the trachea or esophagus or of their relationship to the ETT within them.

Methods that detect the physiological results of moving air through the ETT include 1) observing for the movement of the chest or for distension of the abdomen 2) auscultating the axillae and stomach with a stethoscope and listening for breath sounds emanating from the lungs or for gurgling from the stomach 3) observing for the presence of condensation in the ETT 4) using capnography or capnometry devices that attach to the ETT and detect the presence of carbon dioxide with respiration 5) the use of pulse oximetry to detect the level of oxy-hemoglobin in a patient's blood 6) using microphones and whistles attached to the proximal or distal end of the ETT to detect differences in air flow during spontaneous respiration and/or 7) detecting differences in the precise exhaled oxygen concentrations.

Methods that attempt to detect the location of the ETT using imaging and/or that use the inherent characteristics of the trachea or esophagus or of their relationship to the ETT within them include 8) the use of devices that attach to the proximal end of the ETT and measure the refilling time of a compressed bulb or evacuated syringe 9) rapid inflation and deflation of the airway occlusion cuff (AOC) with palpation of the neck at the suprasternal notch 10) the use of chest x-rays 11) acoustic reflectometry which uses computer analysis of an acoustic impulse echo to reconstruct the anatomy distal to the ETT 12) transtracheal illumination with the use of a lighted stylet 13) detection of the presence of the ETT within the trachea using an ultrasound probe placed on the patient's neck 14) measuring the strength of a magnetic field created between a magnet attached to the distal end of an ETT and one placed over the patient's neck 15) measuring the impedance between two electrodes placed on the patient's chest 16) the use of radio frequency identification (RFID) tags to identify movement of the ETT after correct positioning and/or 17) using a camera built in to the ETT that allows for a continuous video feed of the view from the distal end of the ETT.

The problems associated with the above methods are multiple. Therefore, a need exists for an improved method and device to verify the proper positioning of the ETT.

SUMMARY OF THE PREFERRED EMBODIMENTS

In accordance with a first aspect of the present invention, there is provided an apparatus that includes an endotracheal tube or airway device with one or more lumens having a proximal end and a distal end and one or more airway, esophageal or pharyngeal occlusion cuffs. It will be understood that the term (all of which are referred to herein as an occlusion cuff or airway occlusion cuff or AOC). The airway occlusion cuff includes a sensor for helping determine proper endotracheal tube placement. In a preferred embodiment, the sensor comprises a material that can change its electrical properties in response to a change in pressure, mechanical stress and/or temperature. In another preferred embodiment, the sensor includes a plurality of sensing elements and a display. The display provides visualization of the tissue external to the airway occlusion cuff when the apparatus is in use. The sensor senses the pressure within the airway occlusion cuff and the external pressure applied to the airway occlusion cuff.

In accordance with another preferred embodiment of the present invention, there is provided a method of determining endotracheal tube placement. The method includes the steps of providing an apparatus comprising an endotracheal tube having a proximal end and a distal end, an occlusion cuff and a sensor in the occlusion cuff that has at least one sensing element in electrical communication with a signal processor, inserting the distal end of the endotracheal tube into a patient, inflating the occlusion cuff, wherein an external pressure is applied to the occlusion cuff and sensed by the at least one sensing element, communicating the pressure or mechanical change to the signal processing unit, and displaying the pressure or mechanical change on a display. In a preferred embodiment, each of the sensing elements communicates a pressure or mechanical change to the signal process unit and the pressure or mechanical changes are displayed as an image that is recognizable as the anatomy of the patient. In another preferred embodiment, each of the sensing elements communicates a pressure or mechanical change to the signal process unit, and intermittent pressure variations consistent with the presence of tracheal rings in the tissue surrounding the airway occlusion cuff are shown on the display.

DESCRIPTION OF THE PREFERRED EMBODIMENTS

Figure 1:
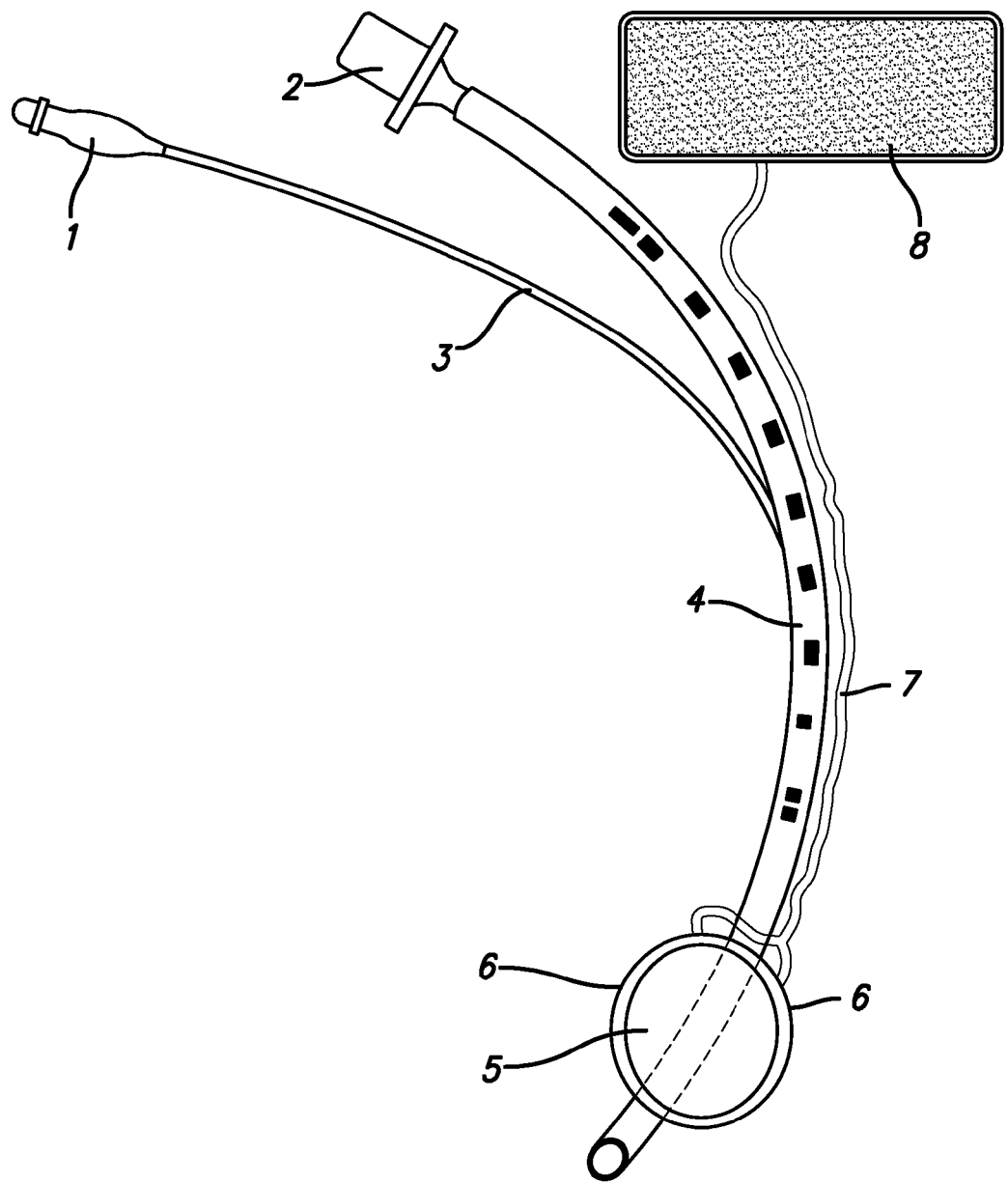
FIG. 1 depicts a lateral view of an endotracheal tube having a sensor in the airway occlusion cuff.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

Embodiments of the present disclosure include systems and methods for imaging endotracheal tube placement, for example, by measuring airway occlusion cuff pressure.

In preparation for surgery or during the resuscitation of a patient, an ETT is often inserted into the trachea to enable oxygen delivery to the patient's lungs. Positioning and placement verification of the ETT generally needs to be accomplished quickly because the brain can become damaged within four minutes without oxygen. Unrecognized misplacement of the ETT in the esophagus can have disastrous consequences, and result in a high incidence of morbidity and mortality.

FIG. 1 depicts a lateral view of an example of a device including an endotracheal tube having a sensor in the airway occlusion cuff.

Figure 2:
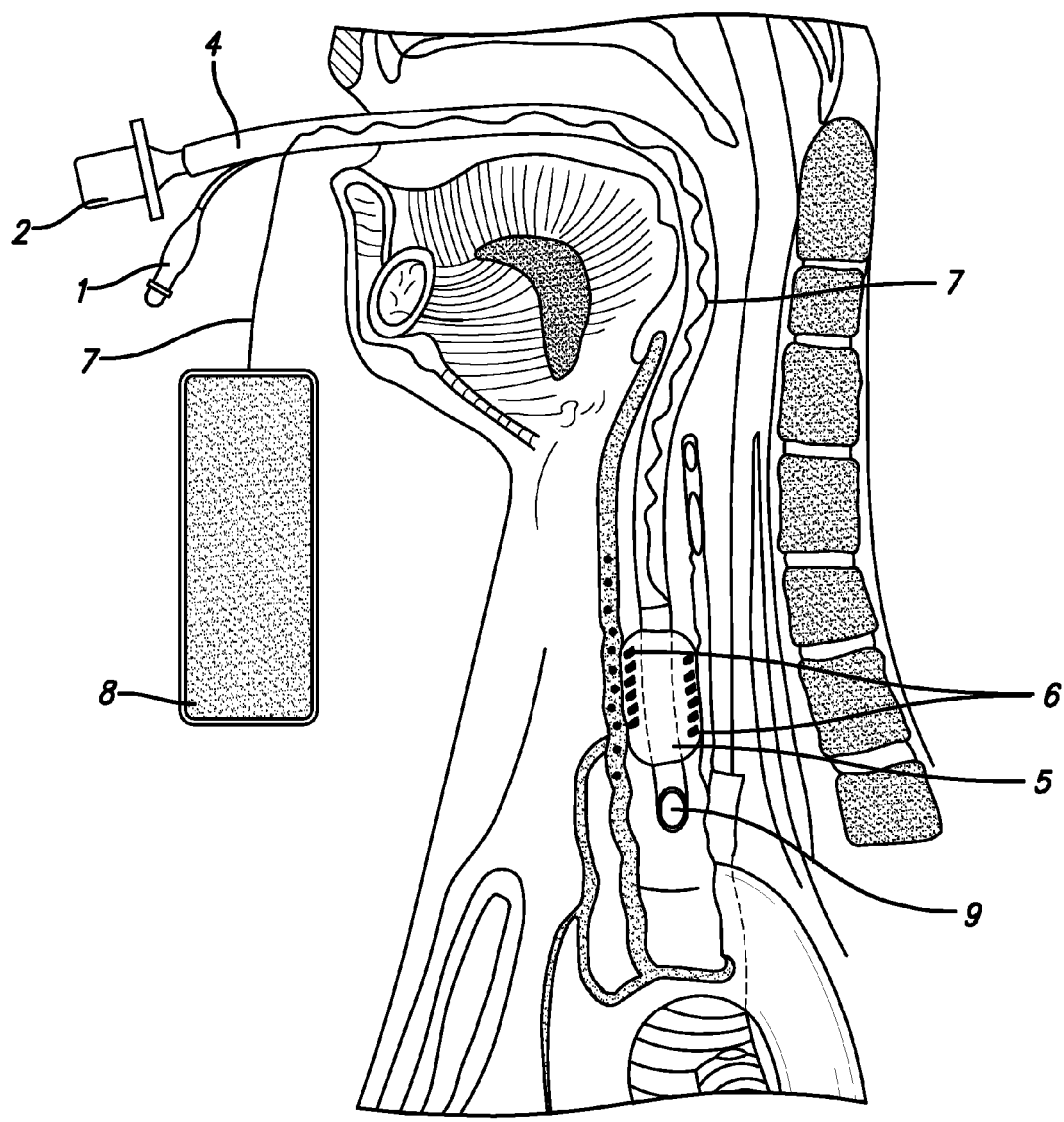
FIG. 2 depicts a lateral view of an endotracheal tube (ETT) having a sensor in the airway occlusion cuff placed properly within the trachea.

FIG. 2 depicts a lateral view of an example of a device including an endotracheal tube (ETT) having a sensor in the airway occlusion cuff placed properly within the trachea.

The device includes an endotracheal tube (4). The endotracheal tube can be a tube of variable size, diameter and/or curvature with a plastic connector on the proximal end (2) that can be connected to a bag-valve mask or ventilator. An airway occlusion cuff (AOC) (5), a circumferential balloon that surrounds the lumen of the ETT (4) near the distal end of the ETT (9), can be connected through small diameter tubing (3) that runs along the length of the ETT (4) to a pilot balloon (1) near the proximal end of the ETT. The pilot balloon (1) can include a one way valve to prevent air from escaping the balloon unless a spring mechanism is depressed by an attached syringe. Air inserted into the pilot balloon (1) at the proximal end of the ETT (4) typically travels through the tubing (3) and inflates the AOC (5).

One embodiment of the device includes a sensor coupled to the ETT. Other sensors may be used to measure the difference between the esophagus and trachea by measuring their vascularity, light reflectivity, thermal characteristics, electromagnetic absorption ranges, longitudinal tissue tensions, laser gauged topographical contours, or direct compliances, or through the use of an elastic bougie attached loosely to the ETT to allow the user to feel the sensation of the tracheal rings at the proximal end of the bougie as the distal end moves over them. For example, a flexible sensor (6) can be integrated into or onto the surface of the AOC (5) or otherwise coupled to the AOC. The sensor (6) can be constructed from any material(s) that can change its electrical properties in response to a change in pressure including but not limited to flexible materials or piezoelectric materials. For example, the sensor (6) can comprise a polyvinylidene fluoride (PVDF) sheet overlaid with an array of electrodes (10). In addition, the sensor can include discrete units of pressure variable resistor ink (PVRI) sandwiched between electrodes spaced at regular intervals (10).

Arrays can employ the piezoelectric properties of materials to convert pressure differences into electrical signals. The electrode array can capture the change in voltage or current generated by the PVDF or PVRI in response to a change in pressure at multiple discrete points or sensing elements (10) along the surface of the AOC (5). The sensing elements (10) may be passive, generating their own electrical signals, or require electricity from an outside source that is then modified by the sensing elements (10). For example, these electrical changes may then either be further modified within the sensor (6) and sent by a wire or series of wires (7) extending from the sensing elements (10) on the AOC (5) along or within the ETT (4) to a signal processing unit (8) or sent directly by a wire (7) to the signal processing unit (8). The signals may also be wirelessly transmitted to the signal processing unit via a wireless connection (e.g., RF, Wifi etc.).

The signal processing unit (8) can receive and process the signals from each sensing element in the array (10) in a controlled manner. The signal processor (8) can amplify and/or filter each signal, and then transfer each signal or a processed version of the signal to a display (8) where it can be converted into a visualization including color wavelength and/or intensity. The display and signal processing unit may be a unitary component (as shown in the figures) or may be separate. Visualizing the pressure contours of the tissue pressed against the AOC allows the user or a computer program to identify that tissue and the corresponding contiguous tracheal, esophageal or pharyngeal structure where the distal ETT is located.

In addition, the force applied by the AOC (5) to the surrounding surface when the AOC is inflated can be determined. In two methods of calculating force as outlined by Choi et al. (Development of Tactile Sensor for Detecting Contact Force and Slip. *International Conference On Intelligent Robots and Systems*. 2005: 1977-1982, the entirety of which is incorporated by reference herein) the surface charge from the piezoelectric phenomena of PVDF is proportional to the applied force in such a way that the strain coefficient for the axis of the applied compressive force over the electroded PVDF area multiplied by the stress applied in the relevant direction equals the surface charge at any one time. A change in force causes a detectable change in charge within the electrode. With respect to PVRI in this example, the pressure applied to the sensor element changes the intrinsic resistance of the ink in such a way that when a fixed input voltage is applied across a film of ink, the output voltage changes in proportion to the force. These translations of change of pressure into electrical signal as sensed by each sensing element can be averaged, (or a maximal change can be determined) and/or compared to a reference force in the form of, as an example, a spring that produces a standard pressure and electrical signal change. In this way, average absolute or maximal AOC pressures can be determined.

Figure 3:
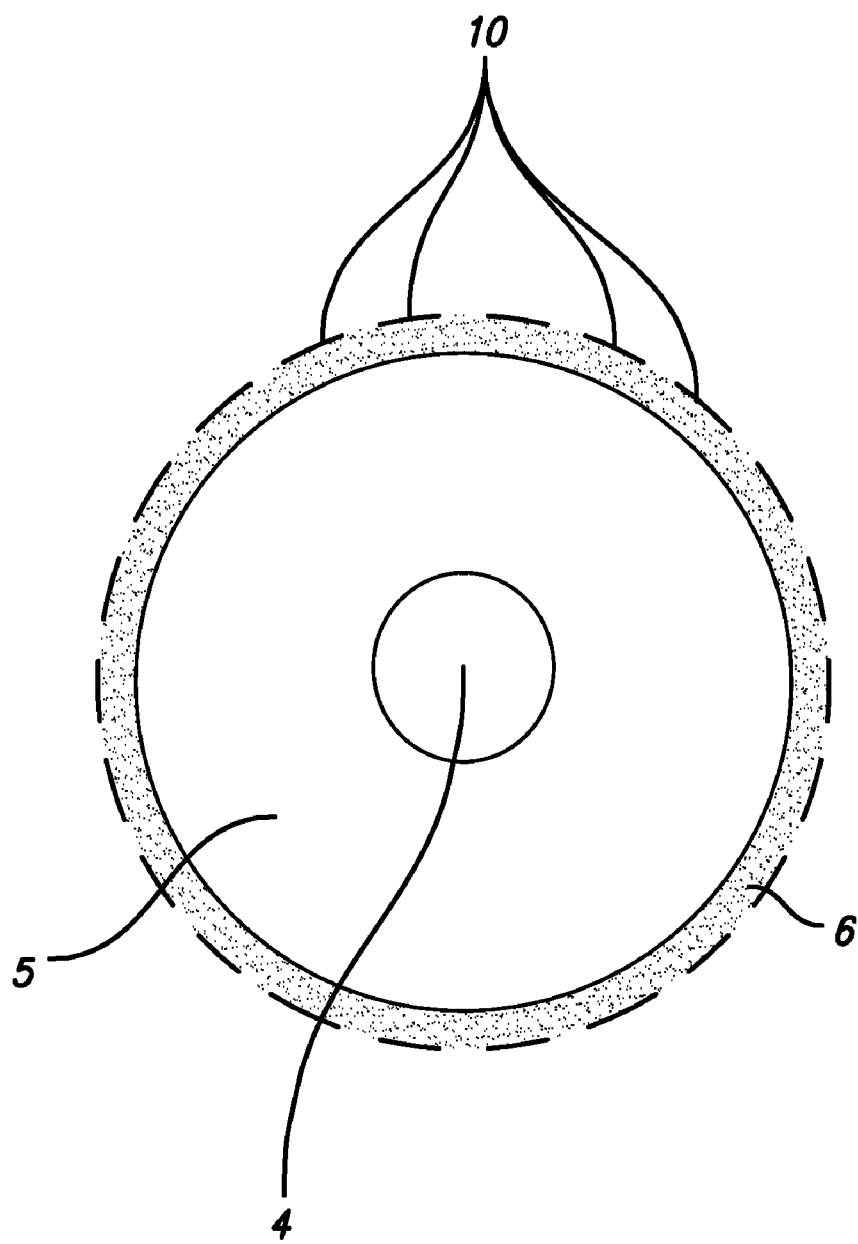
FIG. 3 depicts a cross sectional view of the airway occlusion cuff (AOC), showing the cuff, the sensor and the ETT lumen.

FIG. 3 depicts a cross sectional view of an example of the airway occlusion cuff (AOC) in an endotracheal tube, showing the cuff, the sensor and the ETT lumen.

Figure 4:
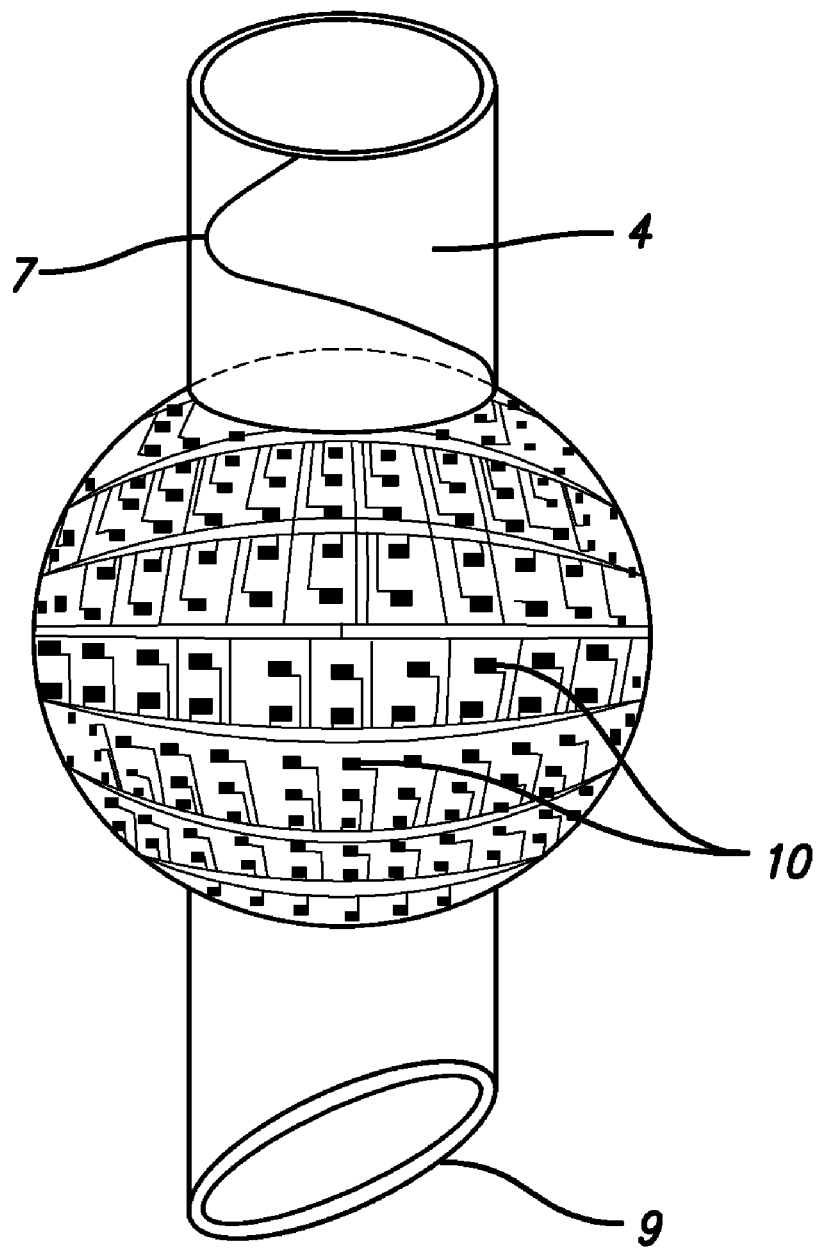
FIG. 4 depicts a three dimensional view of the distal endotracheal tube, the airway occlusion cuff, and incorporated sensor with individual sensing elements.

FIG. 4 depicts a three dimensional view of the distal portion of an example device having an endotracheal tube, the airway occlusion cuff, and incorporated sensor having multiple sensing elements.

In a preferred embodiment, the system/device disclosed herein provides indirect visualization of the tracheal rings, which are key defining features of the trachea. The system/device generally is a fast method of verification of ETT placement. This is because the airway occlusion cuff is inflated prior to providing breaths through the ETT, and verification with indirect visualization of the tracheal rings typically occurs immediately upon cuff inflation. An ETT misplaced in the esophagus can immediately be detected before insufflating the stomach, thereby decreasing the risk of aspirating gastric contents.

In a preferred embodiment, the system/device disclosed herein can be re-usable within a single patient and can provide continuous or repeated confirmation of ETT position. Because the sensor is an element of the cuff and does not impede or rely on airflow, it can be read constantly with consistent quality. Other verification devices are used only during the initial positioning before they are removed and discarded. If the ETT becomes dislodged after the initial placement, the device described here can detect this change in position. The processor and display may be re-usable for multiple patients if it is detachable from the sensor portion of the device. However, this is not a limitation on the present invention.

The system/device disclosed herein verifies ETT positioning within the trachea. Properly placed and functioning carbon dioxide detection devices in healthy patients may provide false positive results when the ETT is positioned too deeply within the trachea and the distal end protrudes into the left or right mainstem bronchus or when the ETT is positioned too shallowly within the hypopharynx, in both these instances, carbon dioxide will be detected with respiration, but the ETT position is not optimal and may be injurious to the patient. In a preferred embodiment, the device described here will indicate, based on anatomy, that an ETT placed in the hypopharynx or a mainstem bronchus is positioned incorrectly.

The system/device disclosed herein can measure an average or maximum absolute pressure exerted by the AOC onto the surrounding tissue, which would allow the medical professional to adjust the volume in the AOC to provide optimal pressure for the patient, reducing the risk of airway tissue damage from high occlusion pressures. This is especially important for patients in which the ETT is in place for long periods of time or in patients where the tissue within the trachea is fragile, such as in infants and children.

In a preferred embodiment, the system/device disclosed here is portable. Its function does not necessarily rely on adjunct devices or heavy, bulky machinery. Although, it may use such machinery in an alternative embodiment. The sensor itself can be incorporated into the ETT, and the attached processor and display can be manufactured to be small, handheld, and lightweight. This portability allows the device to be used in any setting.

The system/device disclosed here does not require significant training or expertise to be used for verification purposes. Although the placement of a standard ETT may require some skill and is generally performed by a medical professional, the interpretation of the displayed data on the device described may be understood by a layman. The data may also be interpretable by software to indicate in a simple manner (e.g. with colored lights [e.g., green and red], tones, or recorded messages) whether the ETT is in the proper position or an improper position, providing a 'yes or no' answer. In this way, this system or a variation thereof may be able to be successfully placed blindly and by a layman either alone or as an adjunct with another device. This feature may also be useful in ICU settings where the position of the ETT can be monitored at all times and appropriate staff alerted when the ETT position changes or the patient prematurely extubates him or herself.

The system/device disclosed herein can monitor the change in status of the trachea over time. During long operations, operations in which significant amounts of fluid were given, operations on the upper airway, or operations in which the patient was prone, the lining of the trachea can become edematous to the extent that its patency is threatened in the absence of an ETT, which can act as a stent. The medical professional must often make decisions about the safety of removing the ETT in this type of situation, with little data to act as a guide. The system/device disclosed here may be able to provide information about how the trachea has changed over time by displaying average or maximum occlusion cuff pressure trends. If the pressure has increased significantly during the course of the procedure, or the pressure displayed when the AOC is maximally deflated is elevated, the medical professional may decide to wait until the AOC pressure returns to baseline.

The disclosed system/device can be supplied to a medical professional or layman who positions the endotracheal tube within the patient and inflates the AOC by injecting air into the pilot balloon. The sensor or sensing elements on the AOC surface generate changes in voltage or current proportional to pressures applied to them and transfer these signals to the signal processing unit which amplifies and filters them and transfers them to the display which converts the signals into an image that can be read and interpreted by the medical professional or layman.

In a preferred embodiment, the system/device disclosed herein does not obstruct or decrease the size of the ETT lumen and does not add "dead space" to the ETT. ETTs that incorporate video cameras must decrease the size of the ETT lumen to accommodate the camera. This decrease in lumen size may impede air flow and significantly increase airway pressures, to the detriment of the patient. 'Dead space' is space within the respiratory tract that does not contribute to gas exchange. Portable capnography devices and some current incarnations of acoustic reflectometry devices add small but significant amounts of dead space to the respiratory tract (especially in children and infants) by increasing the overall length of the ETT. This change in dead space decreases the efficiency of gas exchange.

In a preferred embodiment, the system/device disclosed herein can be modified for use in any type of ETT or balloon incorporating device, including double lumen ETTs and bronchial blockers that are used for thoracic surgery. Its use in these contexts would help an anesthesiologist determine whether the double lumen ETT balloon or bronchial blocker balloon is correctly positioned with the bronchus during the course of the procedure and obviate the need to constantly check ETT position with a fiberoptic bronchoscope.

Figure 5:
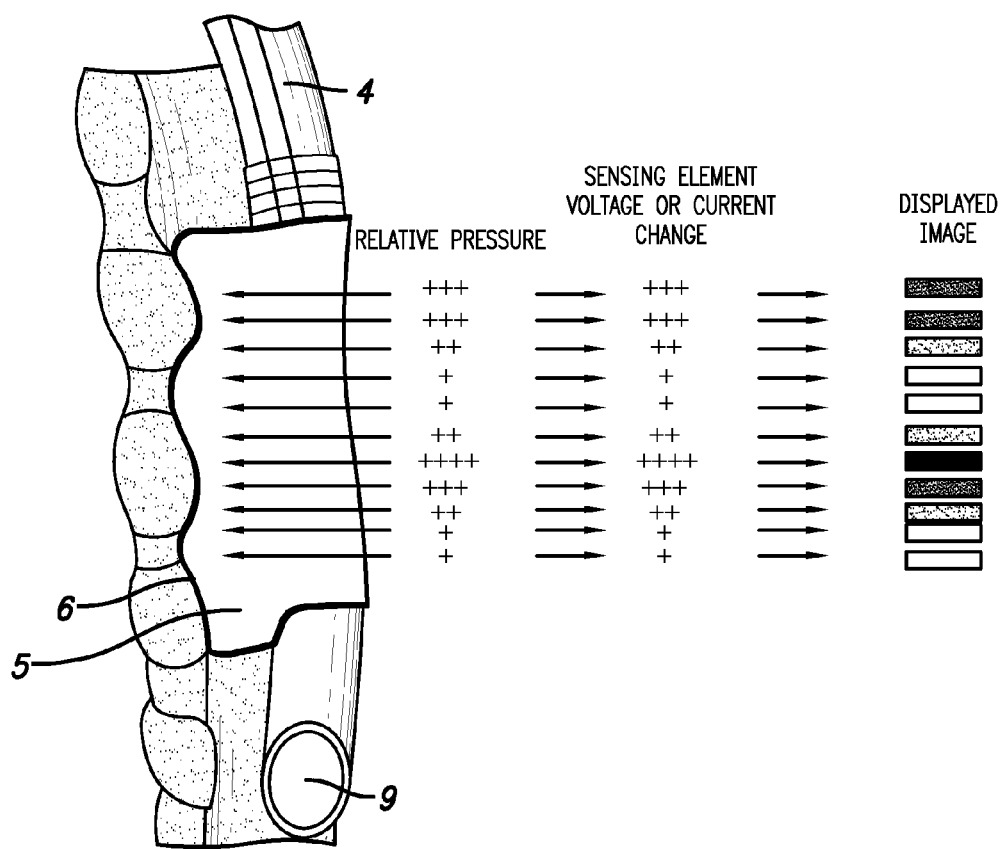
FIG. 5 depicts a cross section of the airway occlusion cuff and sensor interaction with the trachea and the transfer of sensed pressure and contour information to a peripheral device or display.
Figure 6:
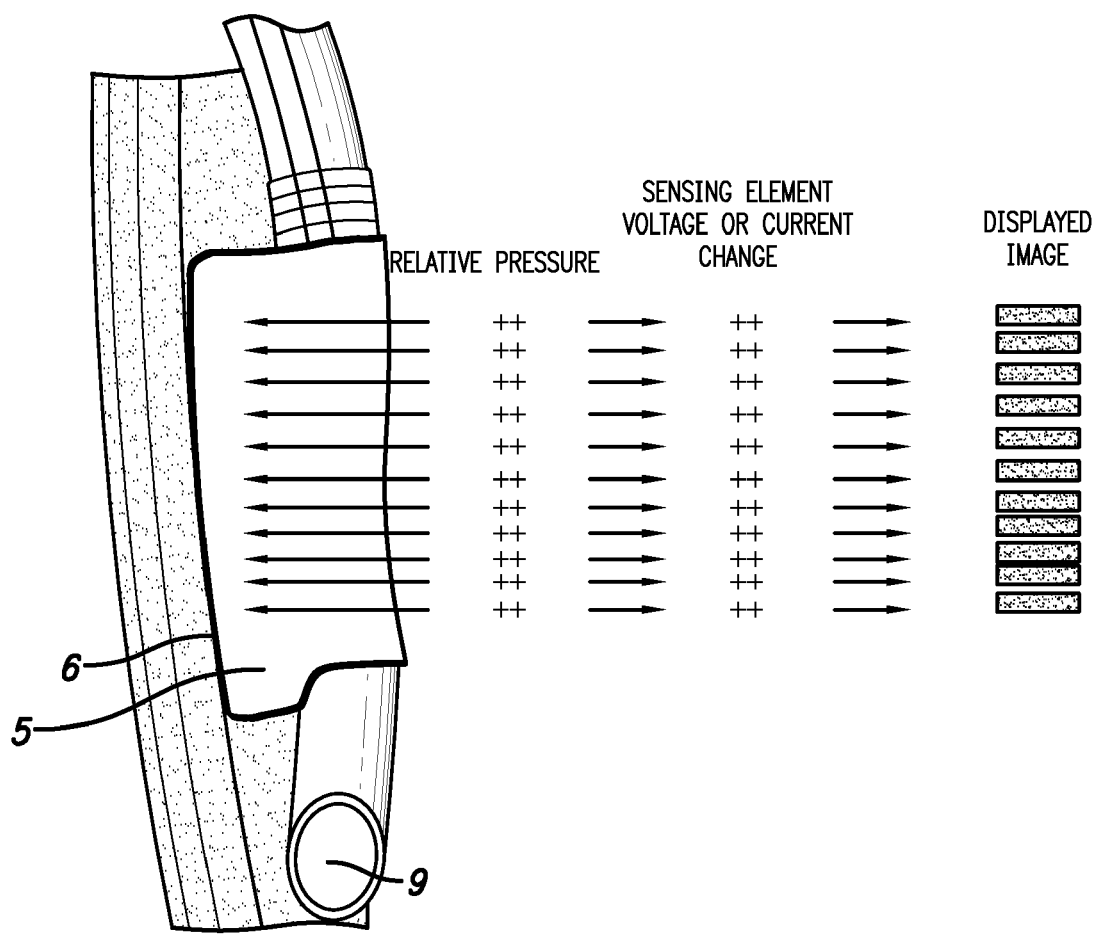
FIG. 6 depicts a cross section of the airway occlusion cuff and sensor interaction with the esophagus and the transfer of sensed pressure and contour information to a. peripheral device or display.

In one embodiment, if the distal ETT is placed in the trachea, the display will show regular intermittent pressure variations consistent with the presence of tracheal rings in the tissue surrounding the AOC. FIG. 5 depicts a cross section of the airway occlusion cuff and sensor interaction with the trachea and the transfer of sensed pressure and contour information to a peripheral device or display, in accordance with a preferred embodiment of the present invention. If the distal ETT is placed in the esophagus, however, the display will not show the regular intermittent pressure variations consistent with the absence of tracheal rings. FIG. 6 depicts a cross section of the airway occlusion cuff and sensor interaction with the esophagus and the transfer of sensed pressure and contour information to a peripheral device or display, in accordance with a preferred embodiment of the present invention. It will be understood that the presence of 360 degree circumferential pressure or mechanical change within the AOC is consistent with the complete occlusion of the anatomical lumen by the AOC.

Figure 7:
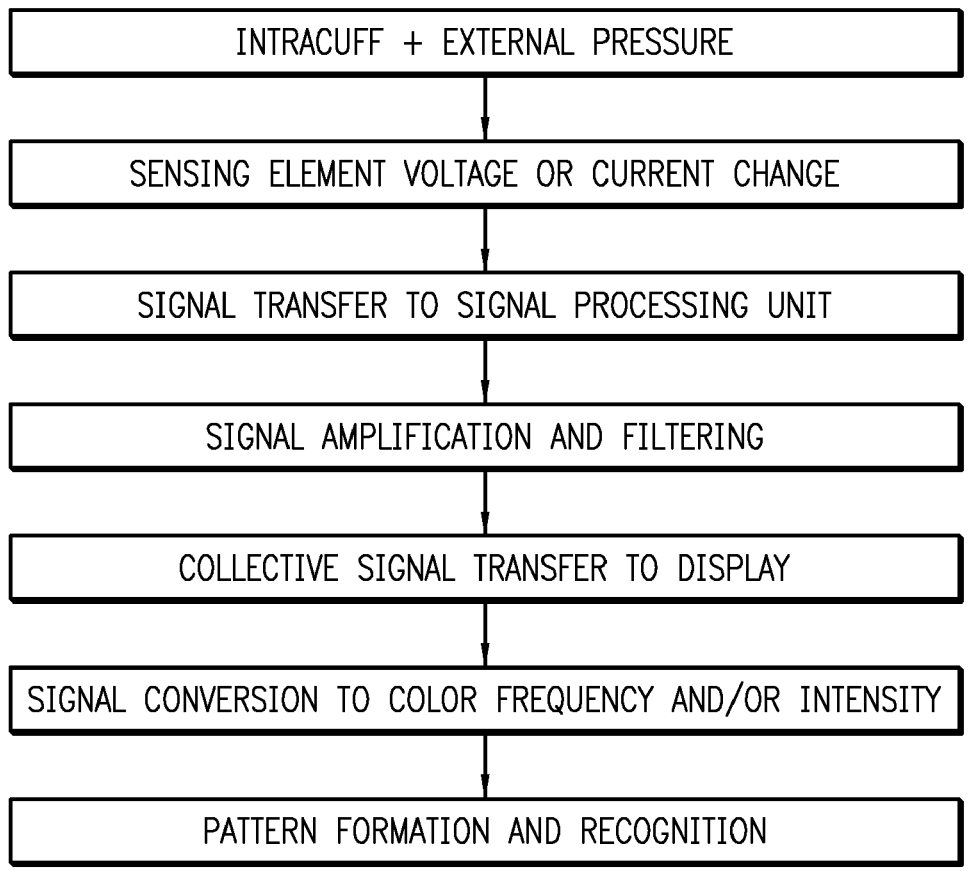
FIG. 7 depicts a flow chart illustrating an example process for using airway occlusion cuff pressure to image endotracheal tube for verification of placement.

FIG. 7 depicts a flow chart illustrating an example process for using airway occlusion cuff pressure to image endotracheal tube for verification of placement.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program, product in a variety of forms, and that the disclosure applies equally regardless of the particular type of machine or computer-readable media used to actually effect the distribution.

Further examples of machine-readable storage media; machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. §112, ¶6, other aspects may likewise be embodied as a means-plus-function claim, or in other forms, such as being embodied in a computer-readable medium. (Any claims intended to be treated under 35 U.S.C. §112, ¶6 will begin with the words "means for"). Accordingly, the applicant reserves the right to add additional claims after filing the application to pursue such additional claim forms for other aspects of the disclosure.

Systems and methods for imaging endotracheal tube placement and/or measuring airway occlusion cuff pressure are disclosed. In one aspect, embodiments of the present disclosure include a system that uses anatomical differences between the trachea and the esophagus to establish the location of the distal end of the endotracheal tube and enables measurement of pressures exerted by the inflated cuff at the distal end of the endotracheal tube on surrounding tissue. The system can determine the placement of the endotracheal tube by indirectly visualizing and thereby identifying the structural differences between the esophagus and the trachea. For example, the system uses a sensor, which may be located on the airway occlusion cuff of the endotracheal tube to identify the presence or absence of the tracheal cartilaginous rings.

What is claimed is:

1. An apparatus comprising an endotracheal tube that defines at least one lumen therein, wherein the tube has a proximal end and a distal end, wherein the tube includes at least one occlusion cuff that includes a sensor that includes a plurality of sensing elements that are in electrical communication with a signal processing unit, wherein the signal processing unit is in electrical communication with a display, wherein each of the sensing elements are adapted to communicate a pressure or mechanical change to the signal processing unit, and wherein the pressure or mechanical changes are displayed as an image that is recognizable as the anatomy of the patient.

2. The apparatus of claim 1 wherein the sensor comprises a material that can change its electrical properties in response to a change in pressure, mechanical stress and/or temperature.

3. The apparatus of claim 2 wherein the sensor comprises a piezoelectric material.

4. The apparatus of claim 2 wherein each sensing element comprises a unit that includes pressure variable resistor ink, and wherein each of the units is disposed between a pair of electrodes.

5. The apparatus of claim 2 wherein each sensing element contains polyvinylidene fluoride and a plurality of electrodes.

6. The apparatus of claim 2 wherein the signal processing unit includes software that processes the data received from the sensor.

7. The apparatus of claim 6 wherein the display provides visualization of the tissue external to the occlusion cuff when the apparatus is in use.

8. The apparatus of claim 6 wherein the display indicates whether the occlusion cuff is in a proper position or an improper position.

9. The apparatus of claim 2 wherein the sensing elements senses the pressure within the occlusion cuff and the external pressure.

10. A method of determining endotracheal tube placement, the method comprising the steps of:
    a) providing an apparatus comprising an endotracheal tube having a proximal end and a distal end, wherein the endotracheal tube includes an occlusion cuff, and wherein the occlusion cuff includes a sensor having a plurality of sensing elements in electrical communication with a signal processor,
    b) inserting the distal end of the endotracheal tube into a patient,
    c) inflating the occlusion cuff,
    d) wherein an external pressure is applied to the occlusion cuff and sensed by at least one of the plurality of sensing elements,
    e) communicating the pressure or a mechanical change to the signal processing unit, and
    f) displaying the pressure or mechanical change on a display, wherein the pressure or mechanical changes are displayed as an image that is recognizable as the anatomy of the patient.

11. The method of claim 10 wherein the sensor includes a plurality of sensing elements, wherein each of the sensing elements communicate a pressure or mechanical change to the signal processing unit, and wherein the presence of 360 degree circumferential pressure or mechanical change within the occlusion cuff is consistent with the complete occlusion of the anatomical lumen by the occlusion cuff.

12. The method of claim 10 wherein the sensor comprises a material that can change its electrical properties in response to a change in pressure, temperature and/or mechanical stress.

13. A method of determining endotracheal tube placement, the method comprising the steps of:
    a) providing an apparatus comprising an endotracheal tube having a proximal end and a distal end, wherein the endotracheal tube includes an occlusion cuff, and wherein the occlusion cuff includes a sensor that includes a plurality of sensing elements in electrical communication with a signal processor,
    b) inserting the distal end of the endotracheal tube into a patient,
    c) inflating the occlusion cuff,
    d) wherein an external pressure is applied to the occlusion cuff and sensed by at least one of the plurality of sensing elements,
    e) communicating the pressure or a mechanical change to the signal processing unit, and
    f) displaying the pressure or mechanical change on a display, wherein intermittent pressure variations consistent with the presence of tracheal rings in the tissue surrounding the airway occlusion cuff are shown on the display.

14. A method of determining endotracheal tube placement, the method comprising the steps of:
    a) providing an apparatus comprising an endotracheal tube having a proximal end and a distal end, wherein the endotracheal tube includes an occlusion cuff, and wherein the occlusion cuff includes a sensor that includes a plurality of sensing elements in electrical communication with a signal processor,
    b) inserting the distal end of the endotracheal tube into a patient, c) inflating the occlusion cuff,
d) wherein an external pressure is applied to the occlusion cuff and sensed by at least one of the plurality of sensing elements,
e) communicating the pressure or a mechanical change to the signal processing unit, and
f) displaying the pressure or mechanical change on a display, and wherein the absence of intermittent mechanical or pressure variations consistent with the esophagus or pharynx in the tissue surrounding the occlusion cuff are shown on the display.

* * * * *